United States Patent

Tancredi et al.

[11] Patent Number: 5,238,845
[45] Date of Patent: Aug. 24, 1993

[54] METHOD FOR PRODUCING A $CO_2$ CALIBRATION LIQUID

[75] Inventors: Gabrio Tancredi; Calzi Claudio, both of Milan, Italy

[73] Assignee: Instrumentation Laboratory S.p.A., Milan, Italy

[21] Appl. No.: 921,560

[22] Filed: Jul. 29, 1992

[30] Foreign Application Priority Data

Aug. 2, 1991 [IT] Italy .................. MI91 A 002177

[51] Int. Cl.⁵ ................ G01N 33/72; G01N 33/96
[52] U.S. Cl. ............................. 436/8; 436/9; 436/11; 436/16; 436/18; 436/19; 436/68; 252/408.1
[58] Field of Search ................. 436/8–19, 436/68, 73–75; 252/408.1

[56] References Cited

U.S. PATENT DOCUMENTS

| | | | |
|---|---|---|---|
| 3,380,929 | 4/1968 | Petersen | 252/408 |
| 3,629,142 | 12/1971 | Marbach | 252/408 |
| 3,681,255 | 8/1972 | Wilfore | 252/408 |
| 4,279,775 | 7/1981 | Louderback et al. | 252/408 |
| 4,753,888 | 6/1988 | Chiang | 436/11 |
| 4,843,013 | 6/1989 | Chiang | 436/11 |
| 4,945,062 | 7/1990 | Chiang | 436/11 |
| 5,013,666 | 5/1991 | Chiang | 436/11 |
| 5,023,186 | 6/1991 | Herring | 436/11 |
| 5,045,529 | 9/1991 | Chiang | 514/6 |
| 5,070,023 | 12/1991 | Calabrese | 436/8 |

*Primary Examiner*—James C. Housel
*Assistant Examiner*—David Redding
*Attorney, Agent, or Firm*—Testa, Hurwitz & Thibeault

[57] ABSTRACT

A method for producing a liquid phase substance having a pre-established concentration of $CO_2$ suitable for calibrating analytical instruments such as hemogasanalyzers consists in:

preparing an aqueous solution of precisely known strength of a water-soluble salt of carbonic acid, then transferring said solution to a flow reactor containing a cation exchange resin in hydrogenionic form, passing the aforesaid solution of carbonic acid salt through the aforesaid cation resin, thereby achieving the reaction of producing a pre-established quantity of $CO_2$, and transferring the eluate thus obtained directly to the analytical instrument for calibration.

9 Claims, No Drawings

METHOD FOR PRODUCING A CO₂ CALIBRATION LIQUID

This invention refers to preparations with a pre-established concentration of $CO_2$, useful in particular for calibrating analytical instruments commonly known as hemogasanalyzers.

The prior known technique suggested obtaining calibration solutions having pre-established $pCO_2$ by using the reaction of calcium bicarbonate with a strong acid, typically hydrochloric or sulphuric acid.

In practice, a bicarbonate solution with a pre-established strength is mixed with a strong acid solution and the $pCO_2$ value in the resulting solution is in pre-established relation with the percentage of bicarbonate. An example of this technique is shown in the Swiss patent 489.018.

The disadvantages presented by the known technique are mainly related to the need to very carefully mix the starting solutions, the volumes of which must be accurately defined, as well as the relative instability of the solutions thus obtained.

The presence of various reagents and gaseous exchanges with the environment also calls for the use of a complex fluidic system.

The scope of the invention is to find a solution to the problem of simple and reliable calibration for the $pCO_2$ canal of a hemogasanalyzer which also simplifies the relative fluidic portion of the instrument, thereby enabling the calibration of instruments using liquid phases with pre-established and stable partial pressures of $CO_2$.

The basic principle of the invention lies in the proposal to generate the species in question ($CO_2$) in an aqueous matrix (or the like) whenever necessary, using separate and per se stable physical-chemical constituents.

Whenever the reaction involved in said generation of $CO_2$ takes place within a controlled physical boundary and is repeatable, it is possible to produce or modify the concentration of $CO_2$ so as to obtain a suitable secondary calibration standard for the analyzer.

Nevertheless, with this invention further considerable advantages are achieved for a $pCO_2$ fluid path compared to that described in the prior art and which can be listed as follows:
single stable reagent
absence of gaseous exchange with the environment
only one species present in the resulting solution, that is $CO_2$
extremely simple fluidics
dependence of the $CO_2$ produced exclusively on the reagent of the starting solution.

In fact, according to the invention, the method for producing a liquid phase calibration substance having a pre-established concentration of $CO_2$ for analytical instruments such as hemogasanalyzers, comprises
preparing an aqueous solution of precisely known strength of an alkali metal salt of carbonic acid (carbonate or bicarbonate);
transferring said solution to a flow reactor containing a cation exchange resin in hydrogenionic form;
passing the aforesaid solution of carbonic acid salt through the aforesaid cation resin, thereby achieving the reaction of producing a pre-established quantity of $CO_2$;
transferring the eluate thus obtained directly to the analytical instrument for calibration.

The scope and features of this invention will be more clearly evident from the following description of an exemplificative embodiment conducted on an instrument manufactured by Instrumentation Laboratory, s.r.l.

To produce the starting solution, use was made of sodium bicarbonate produced by J. T. Baker Chemical Co., although various different commercial sources of said salt can be used, provided the strength of the basic raw material can be measured with absolute precision.

During the course of the test, the concentration of the starting solution used ranged between 1 and 1.5 mM of bicarbonate.

Once the solution has been prepared its strength is ascertained by means of precise analytical techniques known to the average expert in the field and therefore not described in detail.

The solution thus obtained is highly stable, and can therefore be stored in a vessel connected to the measuring instrument. The solution needs to be renewed only for restoring the quantity effectively consumed, without any changes occuring to modify the desired properites of the calibration solution.

The titred solution is transferred from the vessel to an ion-exchange flow reactor, for example by means of a peristaltic pump of known technique.

Said reactor consists essentially of a closed reaction chamber containing an ion-exchange resin in hydrogenionic form, advantageously, but not limitatively, in the form of microspheres. In this form of use (hydrogenionic form), the resin has a greater affinity with the cations of alkali metals.

Each alkali metal cation from the solution, for example of bicarbonate, is consequently exchanged with a hydrogen ion.

The cation of the alkali metal remains attached to the resin. The hydrogen ions produced react quantitatively with the bicarbonate ions to produce carbonic acid which, in the reaction conditions, dissociates completely, for practical purposes, to $CO_2$ and $H_2O$.

The aforementioned sequence of reactions can be diagrammatically described as follows:

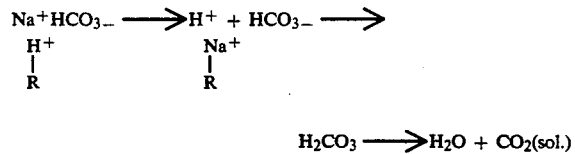

with R indicating the cation resin on which the ion exchange takes place.

Due to the absence of other species in the solution the activity and concentration of the $CO_2$ can be considered as strictly equal.

By generating a solution with an exactly known strength of the $CO_2$ species (gaseous in the conditions of use) under conditions which rule out any possibility of exchange with the environment, it is possible to assign an accurate partial pressure value to said solution in relation to the measurement temperature.

At a given temperature the assigned partial pressure corresponds to that of a hypothetical gaseous phase in equilibrium with the solution. The solution thus obtained presents a slightly acid reaction related to the minute quantity of dissociated carbonic acid.

Since there are no other species capable of taking part in an acid-base equilibrium in the solution, the pH measurement of the latter and the restriction of the pH within very precise limits constitute a reliable verification of the functioning of the reactor.

The solution entering the reactor is, whatever the case may be, (bicarbonate or carbonate) decidedly alkaline, and the measurement at the outlet to the reactor of a pH value in the basic range constitutes positive proof that the reactor is exhausted.

The ion-exchange resin used in this example was the resin AG50W-X2 with a particle size of 100-200 mesh produced by Bio-Rad. This resin is washed thoroughly beforehand with de-ionized water filtered through activated carbon, by stirring and subsequent decantation, for a minimum of three consecutive treatments.

Analytical controls were also carried out on said resin, in order to ascertain its exchange capacity and particle size; these controls are not described here in detail, since they can be identified in a vast range of choice by any average technician in the field.

The aforementioned advantages deriving from the method according to the invention will be clearly evident from the foregoing description, since the concentration of the $CO_2$ produced depends exclusively upon the concentration of the carbonic acid salt used to start with.

We claim:

1. A method for producing a liquid phase calibration substance having a pre-established concentration of $CO_2$, comprising contacting an aqueous solution having a known concentration of an alkali metal salt of carbonic acid with a cation exchange resin wherein said cation is a hydrogen ion.

2. The method of claim 1 wherein the alkali metal salt of carbonic acid is sodium bicarbonate.

3. The method of claim 1 wherein the cation exchange resin is in the form of microspheres.

4. The method of claim 1 wherein the reaction is carried out in a reaction chamber which is closed to the atmosphere.

5. A method for calibrating an instrument which measures the concentration of $CO_2$ in a sample, comprising the steps of:
   a. providing an aqueous solution having a known concentration of an alkali metal salt of carbonic acid;
   b. transferring said solution to an inlet of a flow reactor containing a cation exchange resin, wherein said cation is a hydrogen ion and permitting said solution to pass through said resin to an outlet of said reactor thereby producing a solution containing a known concentration of $CO_2$;
   c. transferring the solution from said outlet directly to said instrument; and
   d. calibrating said instrument.

6. The method of claim 5 wherein steps (b) and (c) are performed in a closed system.

7. The method of claim 5 wherein said alkali metal salt is sodium bicarbonate.

8. The method of claim 5 wherein said outlet of said flow reactor further comprises pH measuring means.

9. The method of claim 5 wherein said cation exchange resin is in the form of microspheres.

* * * * *